United States Patent
Bohlin et al.

(10) Patent No.: US 8,563,755 B2
(45) Date of Patent: Oct. 22, 2013

(54) **PROCESS FOR PREPARING [1S-[1-α, 2-α, 3-β(1S*,2R*) 5-β]]-3-[7-[2-(3,4-DIFLUOROPHENYL)-CYCLOPROPYLAMINO]-5-(PROPYLTHIO)-3H-1,2,3-TRIAZOLO [4,5-D] PYRIMIDIN-3-YL]-5-(2-HYDROXYETHOXY) CYCLOPENTANE-1,2-DIOL AND TO ITS INTERMEDIATES**

(75) Inventors: Martin Hans Bohlin, Södertälje (SE); Helena Hellström, Södertälje (SE); Peter W Johansson, Södertälje (SE); Ulf G Larsson, Södertälje (SE); Mikaela Recknagel, Södertälje (SE); Rhony Aufdenblatten, Visp (CH); Andreas Weiss, Eggerberg (CH); Ursula Weiss, legal representative, Eggerberg (CH)

(73) Assignee: AstraZeneca AB, Sodertalje (SE)

( * ) Notice: Subject to any disclaimer, the term of this patent is extended or adjusted under 35 U.S.C. 154(b) by 70 days.

(21) Appl. No.: 13/062,728

(22) PCT Filed: Sep. 8, 2009

(86) PCT No.: PCT/SE2009/050999
§ 371 (c)(1),
(2), (4) Date: Dec. 13, 2011

(87) PCT Pub. No.: WO2010/030224
PCT Pub. Date: Mar. 18, 2010

(65) Prior Publication Data
US 2012/0101274 A1   Apr. 26, 2012

(60) Provisional application No. 61/095,341, filed on Sep. 9, 2008.

(51) Int. Cl.
*C07D 317/44* (2006.01)

(52) U.S. Cl.
USPC ........................................ 549/437

(58) Field of Classification Search
None
See application file for complete search history.

(56) References Cited

FOREIGN PATENT DOCUMENTS

| EP | 0434450 | 6/1991 |
|---|---|---|
| WO | 0034283 | 6/2000 |
| WO | 0192263 | 12/2001 |
| WO | 02091988 | 11/2002 |
| WO | 2005073213 | 8/2005 |

OTHER PUBLICATIONS

Springthorpe et al., "From ATP to AZD6140: the discovery of an orally active reversible P2Y12 receptor antagonist for the prevention of thrombosis," (2007) Bioorganic Medicinal Chemistry Letters 17:6013-6018.

*Primary Examiner* — Jeffrey Murray
(74) *Attorney, Agent, or Firm* — Pepper Hamilton LLP

(57) ABSTRACT

The present invention is directed to a process for preparing [1S-[1α,2α,3β(1S*,2R*),5β]]-3-[7-[2-(3,4-difluorophenyl)-cyclopropylamino]-5-(propylthio)-3H-1,2,3-triazolo[4,5-d] pyrimidin-3-yl]-5-(2-hydroxyethoxy)cyclopentane-1,2-diol and to intermediates useful in the process.

2 Claims, No Drawings

PROCESS FOR PREPARING [1S-[1-α, 2-α, 3-β(1S*,2R*) 5-β]]-3-[7-[2-(3,4-DIFLUOROPHENYL)-CYCLOPROPYLAMINO]-5-(PROPYLTHIO)-3H-1,2,3-TRIAZOLO [4,5-D] PYRIMIDIN-3-YL]-5-(2-HYDROXYETHOXY) CYCLOPENTANE-1,2-DIOL AND TO ITS INTERMEDIATES

CROSS-REFERENCE TO RELATED APPLICATIONS

This application is the U.S. National Stage filing of International Application Serial No. PCT/SE09/50999 filed Sep. 8, 2009, which claims priority to U.S. Ser. No. 61/095,341 filed Sep. 9, 2008, each of which is incorporated herein by reference in its entirety.

FIELD OF THE INVENTION

The present invention is directed to a process for preparing [1S-[1α,2α,3β(1S*,2R*),5β]]-3-[7-[2-(3,4-difluorophenyl)-cyclopropylamino]-5-(propylthio)-3H-1,2,3-triazolo[4,5-d]pyrimidin-3-yl]-5-(2-hydroxyethoxy)cyclopentane-1,2-diol and to intermediates useful in the process.

BACKGROUND OF THE INVENTION

It has been found that adenosine 5'-diphosphate (ADP) acts as a key mediator of thrombosis. ADP-induced platelet aggregation is mediated by the P2Y12 receptor subtype is located on the platelet membrane. The P2Y12 receptor (also known as $P_{2T}$, $P2Y_{ADP}$ or $P2T_{AC}$) is a G-protein coupled receptor primarily involved in mediating platelet activation/aggregation.

WO99/05143 discloses generically a series of triazolo[4,5-d]pyrimidine compounds having activity as $P_{2T}$ (also known as $P2Y_{12}$, $P2Y_{ADP}$ or $P2T_{AC}$) antagonists. Recently, a new class of direct (non-prodrug) $P_{2T}$ receptor antagonists has been described which offers significant improvements over other anti-thrombotic agents. International Patent Application WO00/34283 discloses novel "direct" $P_{2T}$ receptor antagonists, including the compound of formula (I). WO01/92262 discloses crystalline and amorphous forms of the compound of formula (I).

WO01/92263 discloses a process for preparing [1S-[1α,2α,3β(1S*,2R*),5β]]-3-[7-[2-(3,4-difluorophenyl)-cyclopropylamino]-5-(propylthio)-3H-1,2,3-triazolo[4,5-d]pyrimidin-3-yl]-5-(2-hydroxyethoxy)cyclopentane-1,2-diol (alternatively named (1S,2S,3R,5S)-3-[7-{[(1R,2S)-2-(3,4-Difluorophenyl)cyclopropyl]amino}-5-(propylsulfanyl)-3H-[1,2,3]triazolo[4,5-d]pyrimidin-3-yl]-5-(2-hydroxy-ethoxy)-1,2-cyclopentanediol).

The present invention provides an improved process for preparing a compound of formula (I). In particular, the process according to the present invention provides improved yield of the compound of formula (I) compared to previous processes as well as improved process efficiency and higher purity of the compound of formula (III). A high quality of the compound of formula (I) is obtained without recrystallisation.

OUTLINE OF THE INVENTION

The present invention provides a process for preparing a compound of formula (I)

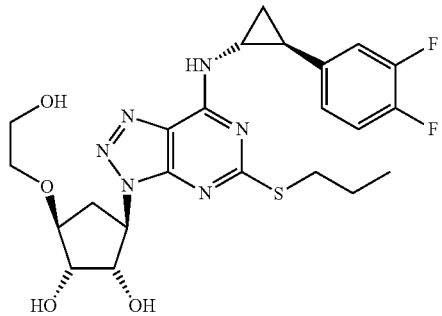

comprising (a) reacting a compound of formula (II)

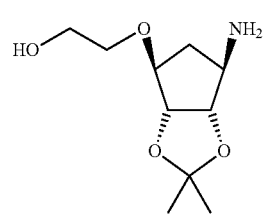

with oxalic acid or dibenzoyl-L-tartaric acid to form the oxalate salt or the dibenzoyl-L-tartrate salt of the compound of formula (II); and (b) reacting the salt of the compound of formula (II) with a compound of formula (VI)

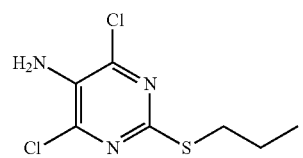

in the presence of a tertiary amine at between 80° and 115° C. at an oxygen concentration below 2.0% by volume, to obtain the compound of formula (III)

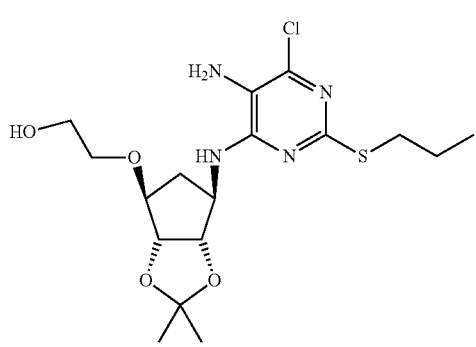

and isolating the compound of formula (III) in crystalline form;

and (c) reacting the compound of formula (III) with acetic acid and sodium nitrite at between 0° C. and 40° C. to obtain the compound of formula (IV)

(IV)

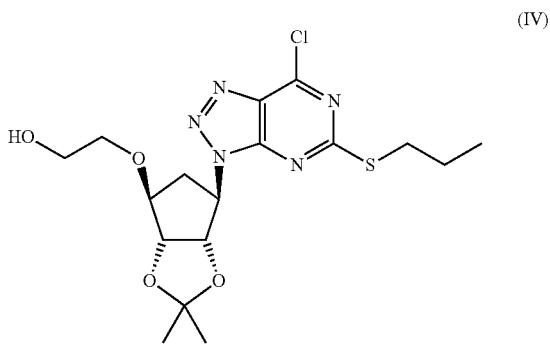

and (d) reacting the compound of formula (IV) with a compound of formula (VII) at a temperature equal to or below 40° C.

(VII)

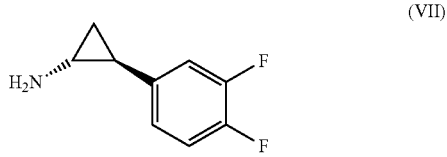

to obtain the compound of formula (V)

(V)

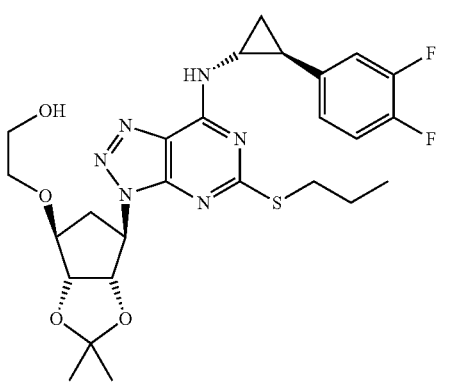

and (e) deprotecting the compound of formula (V) using aqueous hydrochloric acid in methanol in a two-phase system to obtain the compound of formula (I).

The compound of formula (II) can be prepared as described in WO 01/92263 A1.

The compound of formula (VI) can be prepared as described in WO 2005/095358 A2. 4,6-Dichloro-5-nitro-2-(propylthio)pyrimidine may also be reduced to a compound of formula (VI) using methodology described in EP 0931053, EP 0842920 or utilising other types of reagent systems for the reduction of aromatic nitro groups than platinum/vandium combination catalysts, as described for example in R. Larock Comprehensive Organic Transformations, ISBN 0-89573-710-8, VCH Publishers Inc., 1989, page 411.

In one embodiment, step (a) is carried out in ethanol or in a mixture of water and ethanol. In one embodiment, the mixture is heated to about 40-70° C. In one embodiment, oxalic acid is added to the compound of formula (II) and the mixture is heated to about 60-70° C., followed by addition of iso-propylacetate during a period of 1-3 hours and the formed slurry is cooled to about 20-30° C. for about 1-3 hours. In one embodiment, the precipitated solid is isolated before being reacted further.

In one embodiment, step (a) is carried out in ethanol. In one embodiment, step (a) is carried out by adding dibenzoyl-L-tartaric acid to the compound of formula (II) at about 40-60° C. After stirring the mixture for 30 min to 2 hours, the mixture may be cooled to about 5-25° C. for about 1-4 hours. In one embodiment, the precipitated solid is isolated before being reacted further.

Step (b) is carried out at a temperature of 80-115° C. In one embodiment, step (b) is carried out at a temperature of 80-100° C. In one embodiment, the tertiary amine used is triethylamine. In one embodiment, the solvent used in step (b) is selected from ethanol, isopropyl alcohol, ethylene glycol, triethylene glycol, tert-butyl alcohol, iso-butyl alcohol and dimethoxyethane. In one embodiment, the solvent used in step (b) is selected from ethanol, isopropyl alcohol or ethylene glycol. In one embodiment, step (b) is carried out in to ethylene glycol. In one embodiment, the compound of formula (VI) is charged in excess. In one embodiment, the reaction is carried out at atmospheric pressure or at a pressure of 0.5 to 1.5 bar above atmospheric pressure. In one embodiment, the oxygen concentration is below 1.0% by volume. In one embodiment, the oxygen concentration is below 0.5% by volume.

Step (c) is carried out at a temperature of about 0° C. to 40° C. In one embodiment, step (c) is carried out at room temperature, i.e. at 20° C.-30° C. In one embodiment, the reaction is carried out in toluene. In one embodiment, the product of step (c) is used in the subsequent reaction step without isolation. In one embodiment, the toluene solution of the compound of formula (IV) is used directly in the subsequent step, without distillation.

Step (d) is, in one embodiment, carried out at a temperature of about 10-30° C. In one embodiment, the compound of formula (VII) is added to the reaction mixture at a rate that keeps the reaction temperature at or below 30° C. In one embodiment, the product of step (c) is dissolved in toluene. In one embodiment, the compound of formula (VII) is dissolved in aqueous potassium carbonate and the reaction is carried out in a two-phase system. In one embodiment, the product of the reaction of step (d) is washed with acetic acid.

Step (e) is carried out in a two-phase system. In one embodiment, the product of step (d) in toluene is mixed with methanol and concentrated aqueous hydrochloric acid. In one embodiment, $NaHCO_3$ is added to the reaction mixture within 5 hours from the addition of aqueous hydrochloric acid. In one embodiment, the reaction is carried out at a temperature of 10-20° C.

EXAMPLES

Example 1

Preparation of (3aS,4R,6S,6aR)-6-(2-hydroxyethoxy)-2,2-dimethyltetrahydro-3aH-cyclopenta[d][1,3]dioxol-4-aminium oxalate To an ethanol solution of (3 aS,4R,6S,6aR)-6-(2-hydroxyethoxy)-2,2-dimethyltetrahydro-3aH-cyclopenta[d][1,3]dioxol-4-amine (approximately 100 kg in approximately 320 kg of to ethanol, prepared as described in WO01/92263) water (30 kg) was charged. The mixture was heated to 65° C. and oxalic acid×2H$_2$O (57 kg) was added. Iso-propylacetate (665 kg) was added during 2 hours and the resulting slurry was cooled to 20° C. in 2 hours. The cooled slurry was kept at this temperature for additionally 2 hours. The precipitated product was isolated, washed with iso-propylacetate (141 kg) and dried under vacuum to give the title compound as a white solid (116 kg, approximately 82%). $^1$H NMR (400 MHz, DMSO-d6) δ 6.51 (app br s, NH$_2$, COOH and OH protons), 4.70 (app d, J=6 Hz, 1H), 4.61 (app d, J=6 Hz, 1H), 3.91 (app br s, 1H), 3.40-3.59 (m, 5H), 2.12-2.23 (m, 1H), 1.89-2.01 (m, 1H), 1.36 (s, 3H), 1.23 (s, 3H). $^{13}$C NMR (100 MHz, DMSO-d6) δ 164.7, 110.8, 82.8, 82.7, 82.1, 70.5, 60.0, 55.1, 32.5, 26.1, 23.9.

Example 2

Preparation of Bis[(3aS,4R,6S,6aR)-6-(2-hydroxyethoxy)-2,2-dimethyltetrahydro-3aH-cyclopenta[d][1,3]dioxol-4-aminium]2,3-bis(benzoyloxy)succinate To an ethanol solution of dibenzoyl-L-tartaric acid (82 kg in 126 kg of ethanol) a solution of (3aS,4R,6S,6aR)-6-(2-hydroxyethoxy)-2,2-dimethyltetrahydro-3aH-cyclopenta[d][1,3]dioxol-4-amine in ethanol (approximately 100 kg in approximately 320 kg of ethanol, prepared as described in WO01/92263) was added at 50° C. The resulting mixture was stirred for 1 hour at 50° C. and then cooled to 10° C. within 3 hours. The product was isolated, washed with ethanol (150 kg) and dried under vacuum to give the title compound as a white solid (157 kg, approximately 86% yield). $^1$H NMR (400 MHz, DMSO-d6) δ 7.96 (app d, J=8 Hz, 4H), 7.59-7.66 (m, 2H), 7.50, (app t, J=8 Hz, 4H), 5.63 (s, 2H), 4.47-4.57 (m, 4H), 3.73-3.80 (m, 2H), 3.37-3.55 (m, 8H), 3.25-3.34 (m, 2H), 1.93-2.05 (m, 2H), 1.73-1.84 (m, 2H), 1.31 (s, 6H), 1.17 (s, 6H). $^{13}$C NMR (100 MHz, DMSO-d6) δ 168.7, 164.9, 133.0, 130.2, 129.1, 128.4, 110.3, 83.6, 83.2, 82.9, 73.3, 70.3, 60.0, 55.5, 33.1, 26.1, 23.9.

Example 3

Preparation of 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol 4,6-Dichloro-5-nitro-2-(propylthio)pyrimidine (71 kg) and a platinum vanadium catalyst (Platinum vanadium on carbon, 2% Pt and 1% V, 11.15 kg) were charged together with methyl-tert-butylether (298 kg). The mixture was cooled to approximately 5° C. and a hydrogen pressure of 8 bars was applied (the pressure was slowly increased in order to control the exotherm). The reaction mixture was stirred during 9 h at 30° C. and 8 bar hydrogen pressure and the conversion was checked (>99%). The catalyst was filtered off and washed with methyl-tert-butylether (117 kg). The hydrogenation was repeated with a second portion of 4,6-Dichloro-5-nitro-2-(propylthio)pyrimidine (71 kg). The two hydrogenation solutions were combined. Water was separated off and the organic layer was distilled under reduced pressure and at a jacket temperature of 30° C. To the resulting brown oil ethylene glycol (221 kg) was charged and the distillation was continued until no more methyl-tert-butylether was distilling off.

To the ethylene glycol mixture of 4,6-Dichloro-2-(propylthio)pyrimidin-5-amine((3aS,4R,6S,6aR)-6-(2-hydroxyethoxy)-2,2-dimethyltetrahydro-3aH-cyclopenta[d][1,3]dioxol-4-aminium oxalate (118 kg) and triethylamine (161 kg) were added. The resulting reaction mixture was inerted and heated to 100° C. over 3 h and kept at this temperature for 9 h and then cooled to approximately 40° C. Iso-propylacetate (740 kg) and water (644 kg) were added and the mixture was stirred for 30 min at 40° C. The agitation was stopped and the phases allowed to separate, the water layer was sent to waste. The organic layer was washed with water (644 kg), and the phases were again separated. The organic layer was concentrated by vacuum distillation at a jacket temperature of 55° C., in order to remove water; additional portions of iso-propylacetate were added (2×130 kg). When the desired water content was reached the concentration of the 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol was adjusted to approximately 30% (28%) (calculated on 2-[((3aR,4S,6R,6aS)-6-{[5-Amino-6-chloro-2-(propylthio)pyrimidin-4-yl]amino}-2,2-dimethyltetrahydro-3 aH-cyclopenta[d][1,3]dioxol-4-yl)oxy]ethanol). The solution was heated to 62° C. and iso-octane (1150 kg, preheated to 63° C.) was added during 30 minutes. The mixture was seeded with 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol (0.9 kg), agitated at 62° C. during 30 minutes and then cooled to 0° C. in 7 hours. After 1 h at 0° C. the precipitated product was isolated, washed with a pre-cooled (0° C.) mixture of iso-propylacetate (63 kg) and iso-octane (182 kg). Finally the product was washed with iso-octane (232 kg) and dried under vacuum to give the title compound as a white to off-white solid (143 kg, 88%).

Example 4

Preparation of 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol 4,6-Dichloro-5-nitro-2-(propylthio)pyrimidine (600 kg@100%) and a platinum vanadium catalyst (Platinum vanadium on carbon, 2% Pt and 1% V, 46 kg@100%) were charged together with methyl-tert-butylether (2492 kg). A hydrogen pressure of 8 bars was applied over a certain period with parallel heating to 65° C. The reaction mixture was stirred during 3 h at 65° C. and 8 bar hydrogen pressure and the conversion was checked (>99%). The catalyst was filtered off and washed with methyl-tert-butylether (1240 kg). Water was separated off and the organic layer was distilled under reduced pressure and at a jacket temperature of 30° C. To the resulting brown oil ethylene glycol (880 kg) was charged and the distillation was continued until no more methyl-tert-butylether was distilling off. To the ethylene glycol mixture of 4,6-Dichloro-2-(propylthio)pyrimidin-5-amine((3aS,4R,6S,6aR)-6-(2-hydroxyethoxy)-2,2-dimethyltetrahydro-3aH-cyclopenta[d][1,3]dioxol-4-aminium oxalate (530 kg) and triethylamine (707 kg) were added. The resulting reaction mixture was inerted and heated to 100° C. and kept at this temperature for 9 hours and then cooled to approximately 40° C. Iso-propylacetate (3185 kg) and water (2773 kg) were added and the mixture was stirred for 30 min at 40° C. The agitation was stopped and the phases allowed to separate, the water layer was sent to waste. The organic layer was washed with water (2773 kg), and the phases were again separated. The organic layer was concentrated by vacuum distillation at a jacket temperature of 55° C., in order to remove water;

additional portions of iso-propylacetate were added (1706 kg). When the desired water content was reached the concentration of the 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol was adjusted to approximately 27% (calculated on 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol). The solution was heated to 62° C. and iso-octane (5051 kg, pre-heated to 63° C.) was added during 30 minutes. The mixture was seeded with 2-[((3aR, 4S,6R,6aS)-6-{[5-Amino-6-chloro-2-(propylthio)pyrimidin-4-yl]amino}-2,2-dimethyltetrahydro-3 aH-cyclopenta [d][1,3]dioxol-4-yl)oxy]ethanol (0.9 kg), at 62° C. and 58° C. and then cooled to 0° C. in 7 hours. After 1 h at 0° C. the precipitated product was isolated in several centrifuge loads, washed with a pre-cooled (0° C.) mixture of iso-propylacetate and iso-octane. Finally the product was washed with iso-octane and dried under vacuum to give the title compound as a white to off-white solid (610 kg, 84%).

Example 5

Preparation of 2-({(3aR,4S,6R,6aS)-6-[7-Chloro-5-(propylthio)-3H-[1,2,3]triazolo[4,5-d]pyrimidin-3-yl]-2,2-dimethyltetrahydro-3aH-cyclopenta[d][1,3]dioxol-4-yl}oxy)ethanol To 2-[((3 aR,4S,6R,6aS)-6-{[5-Amino-6-chloro-2-(propylthio)-pyrimidin-4-yl]amino}-2,2-dimethyltetrahydro-3 aH-cyclopenta[d][1,3]dioxol-4-yl)oxy]ethanol (180 kg) in toluene (749 kg) and acetic acid (153 kg) were added sodium nitrite (33.2 kg) in water (88 kg) charged with a rate that kept the temperature of the reaction ≤30° C. After the conversion criterion was reached (>99%) potassium carbonate (176 kg) in water (360 kg) was added to the reaction solution whereafter the water layer was separated off and the organic-layer was used in the next step.

Example 6

Preparation of 2-({(3aR,4S,6R,6aS)-6-[7-chloro-5-(propylthio)-3H-[1,2,3]-triazolo[4,5-d]pyrimidin-3-yl]-2,2-dimethyltetrahydro-3aH-cyclopenta[d][1,3]dioxol-4-yl}oxy)ethanol 2-[((3aR,4S,6R,6aS)-6-{[5-Amino-6-chloro-2-(propylthio)pyrimidin-4-yl]amino}-2,2-dimethyl-tetrahydro-3aH-cyclopenta[d][1,3]dioxol-4-yl)oxy]ethanol (320 kg) and sodium nitrite (61 kg) were dissolved in a mixture of water (224 kg) and toluene (1450 kg) at room temperature. Acetic acid (276 kg) was charged with a rate that kept the temperature of the reaction ≤30° C. After full conversion was reached (≥99.9%), potassium carbonate (317 kg) dissolved in water (640 kg) was added to the reaction solution. After the extraction the water layer was separated off and the organic layer was used in the next step.

Example 7

Preparation of 2-({(3aR,4S,6R,6aS)-6-[7-{[(1R,2S)-2-(3,4-Difluorophenyl)cyclopropyl]amino}-5-(propylthio)-3H-[1,2,3]triazolo[4,5-d]pyrimidin-3-yl]-2,2-dimethyltetrahydro-3aH-cyclopenta[d][1,3]dioxol-4-yl}oxy)ethanol trans-(1R,2S)-2-(3,4-Difluorophenyl)cyclopropan-aminium (2R)-2-hydroxy-2-phenylethanoate (146 kg, prepared as described in WO2008/018822, WO2008/018823, WO01/92200) and potassium carbonate (156 kg) were dissolved in water (576 kg) and charged to the 2-({(3aR,4S,6R,6aS)-6-[7-Chloro-5-(propylthio)-3H-[1,2,3]triazolo[4,5-d]pyrimidin-3-yl]-2,2-dimethyltetrahydro-3 aH-cyclopenta[d][1,3]dioxol-4-yl}oxy)ethanol solution with a rate that kept the temperature of the reaction ≤30° C. After the conversion criterion was reached (>99%) the water layer was separated off. The organic layer was washed twice with acetic acid (18 kg) and sodium chloride (13 kg) in water (560 kg) and then twice with sodium chloride (54 kg) in water (438 kg), whereafter the organic layer was used in the next step.

Example 8

Preparation of 2-({(3aR,4S,6R,6aS)-6-[7-{[(1R,2S)-2-(3,4-difluorophenyl)-cyclopropyl]amino}-5-(propylthio)-3H-[1,2,3]triazolo[4,5-d]pyrimidin-3-yl]-2, 2-dimethyl-tetrahydro-3aH-cyclopenta[d][1,3] dioxol-4-yl}oxy)ethanol trans-(1R,2S)-2-(3,4-Difluorophenyl)cyclopropan-aminium (2R)-2-hydroxy-2-phenylethanoate (258 kg) and potassium carbonate (280 kg) were dissolved in water (1024 kg) and charged to the solution of 2-({(3aR,4S,6R,6aS)-6-[7-chloro-5-(propylthio)-3H-[1,2,3]triazolo[4,5-d]pyrimidin-3-yl]-2,2-dimethyltetrahydro-3aH-cyclopenta[d][1,3]dioxol-4-yl}oxy)ethanol solution from example 5 above with a rate that kept the temperature of the reaction ≤30° C. After full conversion was reached (≥99.9%) the water layer was separated off. The organic layer was washed with a mixture of acetic acid (96 kg) and sodium chloride (96 kg) in water (768 kg) and then washed again with a mixture of acetic acid (32 kg) and sodium chloride (22 kg) in water (952 kg). A third wash of the organic layer was done with sodium chloride (96 kg) in water (864 kg), whereafter the organic layer was used in the next step.

Example 9

Preparation of [1S-[1α,2α,3β(1S*,2R*),5β]]-3-[7-[2-(3,4-difluorophenyl)-cyclopropylamino]-5-(propylthio)-3H-1,2,3-triazolo[4,5-d]pyrimidin-3-yl]-5-(2-hydroxyethoxy)cyclopentane-1,2-diol The 2-({(3aR,4S,6R,6aS)-6-[7-{[(1R,2S)-2-(3,4-Difluorophenyl)cyclopropyl]amino}-5-(propylthio)-3H-[1,2,3]triazolo[4,5-d]pyrimidin-3-yl]-2,2-dimethyltetrahydro-3aH-cyclopenta[d][1,3]dioxol-4-yl}oxy)ethanol solution from above was cooled to 15° C., a solution of concentrated aqueous hydrochloric acid (465 kg) in methanol (623 kg), also tempered to 15° C., was charged. The reaction was stirred at 15° C. until the conversion criterion was fulfilled (>97%) and the phases were allowed to separate. The methanol-water layer, containing the product, was added to sodium bicarbonate (404 kg) in water (749 kg), keeping the temperature below 22° C. When pH≥6 the aqueous layer was extracted with ethylacetate (756 kg) and the phases were separated. The water layer was again washed with ethylacetate (1080 kg) whereafter the aqueous layer was discharged. The ethylacetate layers were combined and washed once with water (490 kg). The water content in the remaining ethylacetate solution was decreased to ≤0.8% (w/w) by vacuum distillation at 50° C., followed by a clear filtration and the concentration was adjusted to 6.2 L/kg 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol. The mixture was heated to 50° C. and then iso-octane was added (1152 kg) during 45 minutes. The slurry was cooled to 0° C. during 2.5 hours and then kept at this temperature for 3.5 hours. The product was isolated and washed with a cold (<5° C.) mixture of ethylacetate (722 kg) and iso-octane (828 kg). Finally, the isolated product was dried under vacuum to give the title compound as a white solid (203 kg, 90% calculated from 2-[((3aR,4S,6R,6aS)-6-{[5-Amino-6-chloro-2-(propylthio)pyrimidin-4-yl]amino}-2,2-dimethyltetrahydro-3aH-cyclopenta[d][1,3]dioxol-4-yl)oxy]ethanol).

Example 10

Preparation of [1S-[1α,2α,3β(1S*,2R*),5β]]-3-[7-[2-(3,4-difluorophenyl)-cyclopropylamino]-5-(propylthio)-3H-1,2,3-triazolo[4,5-d]pyrimidin-3-yl]-5-(2-hydroxyethoxy)cyclopentane-1,2-diol A solution of 2-({(3aR,4S,6R,6aS)-6-[7-{[(1R,2S)-2-(3,4-difluorophenyl)cyclopropyl]amino}-5-(propylthio)-3H-[1,2,3]triazolo[4,5-d]pyrimidin-3-yl]-2,2-dimethyltetrahydro-3aHcyclopenta[d]-[1,3]dioxol-4-yl}oxy)ethanol (430 kg) in toluene (1448 kg) was cooled to 15° C. A solution of concentrated aqueous hydrochloric acid (831 kg) in methanol (933 kg), also cooled to 15° C., was charged and the reaction mixture was agitated vigorously at 15° C. for 2 h before the two phases were allowed to separate. The methanol/water layer, containing the product, was added to a slurry of sodium bicarbonate (745 kg) in water (1024 kg) while keeping the temperature between 15-25° C. The pH gained was pH 8 after completion of the quench (criterion pH≥6) and the aqueous layer was then extracted with ethyl acetate (969 kg). The ethyl acetate phase and some of the water phase was transferred by decantation to another reactor. The water layer was washed a second time with ethyl acetate (289 kg) and this second ethyl acetate phase and some of the water phase was transferred by decantation to another reactor. The water layer was washed a third time with ethyl acetate (289 kg) and this third ethyl acetate phase and some of the water phase was transferred by decantation to another reactor. The phases were separated and the water phase was discarded. The ethyl acetate phase was washed with a solution of sodium chloride (150 kg) dissolved in water (434 kg). The mixture was stirred for 30 min at 24° C. after which the stirring was stopped and the phases were allowed to separate. The water phase was then discarded and more ethyl acetate (1556 kg) was charged to the ethyl acetate phase at 24° C. The mixture was filtered through charcoal filter plates followed by a filter with K200 paper filter plates. The filters were washed with ethyl acetate (492 kg) at 24° C. and this washing portion was pooled with the filtered ethyl acetate solution. The water content in the ethyl acetate solution was decreased further to 0.4% w/w by vacuum distillation at 50° C. and the volume was adjusted to 2200 L (criterion 6.88 L/kg 2-[((3aR,4S,6R,6aS)-6-{[5-amino-6-chloro-2-(propylthio)pyrimidin-4-yl]amino}-2,2-dimethyltetrahydro-3 aH-cyclopenta[d][1,3]dioxol-4-yl)oxy]ethanol). The mixture was heated to 57° C. to obtain a clear solution and it was then cooled to 50° C. before addition of iso-octane (1435 kg) over 1.72 h. The obtained slurry was cooled to 0° C. over 2.35 h and then kept at this temperature for 2.33 h. The product was isolated and washed with a cold (about 0° C.) mixture of ethyl acetate (828 kg) and iso-octane (724 kg). Finally, the isolated product was dried under vacuum at 40° C. to give the title compound as a white solid (328 kg, 82% calculated from 2-[((3aR,4S,6R,6aS)-6-{[5-amino-6-chloro-2-(propylthio)pyrimidin-4-yl]amino}-2,2-dimethyltetrahydro-3aH-cyclopenta[d][1,3]dioxol-4-yl) oxy]ethanol).

Calculation of Yield

| | Starting material | Product | Yield |
| --- | --- | --- | --- |
| WO01/92263 | 2-{[(3aR,4S,6R,6aS)-6-amino-2,2-dimethyltetrahydro-3aH-cyclopenta[d][1,3]-dioxol-4-yl]oxy}-1-ethanol, L-tartaric acid salt (1:1) | [1S-[1α,2α,3β(1S*,2R*),5β]]-3-[7-[2-(3,4-difluorophenyl)-cyclopropylamino]-5-(propylthio)-3H-1,2,3-triazolo[4,5-d]pyrimidin-3-yl]-5-(2-hydroxyethoxy) cyclopentane-1,2-diol | 55% |
| Present invention | (3aS,4R,6S,6aR)-6-(2-hydroxyethoxy)-2,2-dimethyltetrahydro-3aH-cyclopenta[d][1,3]dioxol-4-aminium oxalate | [1S-[1α,2α,3β(1S*,2R*),5β]]-3-[7-[2-(3,4-difluorophenyl)-cyclopropylamino]-5-(propylthio)-3H-1,2,3-triazolo[4,5-d]pyrimidin-3-yl]-5-(2-hydroxyethoxy) cyclopentane-1,2-diol | 79% |

The invention claimed is:
1. A compound selected from the oxalate salt or the dibenzoyl-L-tartrate salt of the compound of formula (II)

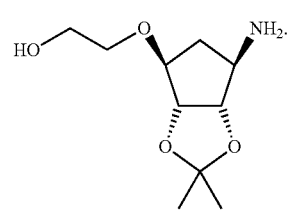

2. A process for preparing an oxalate salt or a dibenzoyl-L-tartrate salt of the compound of formula (II)

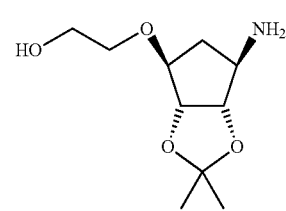

wherein the compound of formula (II) is reacted with oxalic acid or dibenzoyl-L-tartaric acid to form the oxalate salt or the dibenzoyl-L-tartrate salt.

* * * * *